(12) United States Patent
Mills et al.

(10) Patent No.: US 8,096,691 B2
(45) Date of Patent: Jan. 17, 2012

(54) OPTICAL IRRADIATION DEVICE

(75) Inventors: Robin Walter Mills, Wiltshire (GB); Klaus Dieter Jandt, Bristol (GB)

(73) Assignee: Koninklijke Philips Electronics N V, Eindhoven (NL)

( * ) Notice: Subject to any disclaimer, the term of this patent is extended or adjusted under 35 U.S.C. 154(b) by 0 days.

(21) Appl. No.: 12/627,461

(22) Filed: Nov. 30, 2009

(65) Prior Publication Data

US 2010/0073957 A1    Mar. 25, 2010

Related U.S. Application Data

(62) Division of application No. 09/509,433, filed as application No. PCT/GB98/02905 on Sep. 25, 1998, now Pat. No. 7,645,056.

(30) Foreign Application Priority Data

Sep. 25, 1997 (GB) .................................. 9720443.2
Mar. 20, 1998 (GB) .................................. 9806046.0

(51) Int. Cl.
*H01L 33/00* (2010.01)

(52) U.S. Cl. ... 362/555; 362/573; 362/800; 362/249.02; 362/235

(58) Field of Classification Search ............. 362/311.02, 362/800, 555, 573, 574, 249.02, 235, 157; 385/121, 115, 134; 433/29, 215
See application file for complete search history.

(56) References Cited

U.S. PATENT DOCUMENTS

| | | | |
|---|---|---|---|
| 398,383 | A | 2/1889 | Crommer |
| 3,327,712 | A | 6/1967 | Kaufman et al. |
| 3,512,027 | A | 5/1970 | Kupsky |
| 3,548,930 | A | 12/1970 | Byrd |
| 3,603,382 | A | 9/1971 | Paine et al. |
| 3,638,013 | A | 1/1972 | Keller |
| 3,677,329 | A | 7/1972 | Kirkpatrick |
| 3,681,592 | A | 8/1972 | Hugelshofer |
| 3,712,984 | A | 1/1973 | Lienhard |
| 3,714,981 | A | 2/1973 | Noren |
| 3,733,481 | A | 5/1973 | Kuyt |
| 3,811,493 | A | 5/1974 | Bilinski et al. |

(Continued)

FOREIGN PATENT DOCUMENTS

CA    2190225    6/1997

(Continued)

OTHER PUBLICATIONS

LumiLeds Lighting LLC, "Lumen Maintenance of White Luxeon™ Power Light Sources," Application Brief AB07, LumiLeds Lighting, US LLC 2006.

(Continued)

*Primary Examiner* — Anabel Ton
(74) *Attorney, Agent, or Firm* — Lando & Anastasi, LLP

(57) ABSTRACT

An optical irradiation device incorporating a cluster of LEDs arranged so that shaped facets of adjacent LEDs come together to increase the packing density of LEDs in the cluster. A light guide collects light emitted by the LEDs. Two or more light guides and LED clusters may be arranged in series to produce a single light beam. A heat pipe is provided to conduct heat away from the LEDs. The heat pipe may be annular and contain an inner storage space for batteries or the like.

26 Claims, 4 Drawing Sheets

U.S. PATENT DOCUMENTS

| | | | |
|---|---|---|---|
| 3,868,513 A | 2/1975 | Gonser | |
| 3,872,463 A | 3/1975 | Lapeyre | |
| 3,952,798 A | 4/1976 | Jacobson et al. | |
| 3,970,856 A | 7/1976 | Mahaffey et al. | |
| 4,048,490 A | 9/1977 | Troue | |
| 4,114,274 A | 9/1978 | Jones | |
| 4,114,946 A | 9/1978 | Hoffmeister et al. | |
| 4,149,086 A | 4/1979 | Nath | |
| 4,184,196 A | 1/1980 | Moret et al. | |
| 4,185,891 A | 1/1980 | Kaestner | |
| 4,186,748 A | 2/1980 | Schlager | |
| 4,209,907 A | 7/1980 | Tsukada et al. | |
| 4,229,658 A | 10/1980 | Gonser | |
| 4,230,453 A | 10/1980 | Reimers | |
| 4,233,649 A | 11/1980 | Scheer et al. | |
| 4,280,273 A | 7/1981 | Vincent | |
| 4,298,806 A | 11/1981 | Herold | |
| 4,337,759 A | 7/1982 | Popovich et al. | |
| 4,346,329 A | 8/1982 | Schmidt | |
| 4,385,344 A | 5/1983 | Gonser | |
| 4,391,588 A | 7/1983 | Matsui | |
| 4,398,885 A | 8/1983 | Loge et al. | |
| 4,412,134 A | 10/1983 | Herold et al. | |
| 4,445,858 A | 5/1984 | Johnson | |
| 4,450,139 A | 5/1984 | Bussiere et al. | |
| 4,610,630 A | 9/1986 | Betush | |
| 4,666,406 A | 5/1987 | Kanca, III | |
| 4,671,349 A | 6/1987 | Wolk | |
| 4,673,353 A | 6/1987 | Nevin | |
| 4,675,785 A | 6/1987 | Young | |
| 4,716,296 A | 12/1987 | Bussiere et al. | |
| 4,729,076 A | 3/1988 | Masami et al. | |
| 4,742,432 A | 5/1988 | Thillays et al. | |
| 4,757,381 A | 7/1988 | Cooper et al. | |
| 4,791,634 A | 12/1988 | Miyake | |
| 4,792,692 A | 12/1988 | Herold et al. | |
| 4,810,194 A | 3/1989 | Snedden | |
| 4,822,335 A | 4/1989 | Kawai et al. | |
| 4,826,431 A | 5/1989 | Fujimura et al. | |
| 4,836,782 A | 6/1989 | Gonser | |
| 4,839,566 A | 6/1989 | Herold et al. | |
| 4,845,405 A | 7/1989 | Yamane et al. | |
| 4,846,546 A | 7/1989 | Cuda | |
| 4,857,801 A | 8/1989 | Farrell | |
| 4,888,489 A | 12/1989 | Bryan | |
| 4,893,354 A | 1/1990 | Janzen et al. | |
| 4,901,324 A | 2/1990 | Martin | |
| 4,935,665 A | 6/1990 | Murata | |
| 4,936,808 A | 6/1990 | Lee | |
| 4,948,215 A | 8/1990 | Friedman | |
| 4,963,798 A | 10/1990 | McDermott | |
| 4,999,310 A | 3/1991 | Kim | |
| 5,003,434 A | 3/1991 | Gonser et al. | |
| 5,007,837 A | 4/1991 | Werly | |
| 5,017,140 A | 5/1991 | Ascher | |
| 5,029,335 A | 7/1991 | Fisher et al. | |
| 5,029,957 A | 7/1991 | Hood | |
| 5,046,840 A | 9/1991 | Abbiss et al. | |
| 5,070,258 A | 12/1991 | Izumi et al. | |
| 5,099,399 A | 3/1992 | Miller et al. | |
| 5,115,761 A | 5/1992 | Hood | |
| 5,147,204 A | 9/1992 | Patten et al. | |
| 5,150,016 A | 9/1992 | Sawase et al. | |
| 5,160,200 A | 11/1992 | Cheselske | |
| 5,161,879 A | 11/1992 | McDermott | |
| 5,162,696 A | 11/1992 | Goodrich | |
| 5,169,632 A | 12/1992 | Duell et al. | |
| 5,173,810 A | 12/1992 | Yamakawa | |
| 5,195,102 A | 3/1993 | McLean et al. | |
| 5,198,678 A | 3/1993 | Oppawsky | |
| 5,201,655 A | 4/1993 | Friedman | |
| 5,233,283 A | 8/1993 | Kennedy | |
| 5,242,602 A | 9/1993 | Richardson et al. | |
| 5,253,260 A | 10/1993 | Palombo | |
| 5,265,792 A | 11/1993 | Harrah et al. | |
| 5,268,812 A | 12/1993 | Conte | |
| 5,278,629 A | 1/1994 | Schlager et al. | |
| 5,283,425 A | 2/1994 | Imamura | |
| 5,290,169 A | 3/1994 | Friedman et al. | |
| 5,301,090 A * | 4/1994 | Hed | 362/558 |
| 5,302,124 A | 4/1994 | Lansing et al. | |
| 5,309,457 A | 5/1994 | Minch | |
| 5,312,249 A | 5/1994 | Kennedy | |
| 5,316,473 A | 5/1994 | Hare | |
| 5,328,368 A | 7/1994 | Lansing et al. | |
| 5,371,753 A | 12/1994 | Adsett | |
| 5,371,826 A | 12/1994 | Friedman | |
| 5,373,114 A | 12/1994 | Kondo et al. | |
| 5,387,800 A | 2/1995 | Kurtich et al. | |
| 5,418,384 A | 5/1995 | Yamana et al. | |
| 5,420,768 A | 5/1995 | Kennedy | |
| 5,445,608 A | 8/1995 | Chen et al. | |
| 5,457,611 A | 10/1995 | Verderber | |
| 5,471,129 A | 11/1995 | Mann | |
| 5,474,449 A | 12/1995 | Loge et al. | |
| 5,487,662 A | 1/1996 | Kipke et al. | |
| 5,504,764 A | 4/1996 | Pohlmann et al. | |
| 5,521,392 A | 5/1996 | Kennedy et al. | |
| 5,522,225 A | 6/1996 | Eskandari | |
| 5,530,632 A | 6/1996 | Shikano et al. | |
| 5,535,230 A | 7/1996 | Abe | |
| 5,554,855 A | 9/1996 | Ueno | |
| 5,616,141 A | 4/1997 | Cipolla | |
| 5,617,492 A | 4/1997 | Beach et al. | |
| 5,631,987 A | 5/1997 | Lasky et al. | |
| 5,634,711 A | 6/1997 | Kennedy et al. | |
| 5,660,461 A | 8/1997 | Ignatius et al. | |
| 5,664,042 A | 9/1997 | Kennedy | |
| 5,664,864 A | 9/1997 | Kuth | |
| 5,698,866 A | 12/1997 | Doiron et al. | |
| 5,707,139 A | 1/1998 | Haitz | |
| 5,711,665 A | 1/1998 | Adam et al. | |
| 5,729,561 A | 3/1998 | Hironaka | |
| 5,747,363 A | 5/1998 | Wei et al. | |
| 5,759,032 A | 6/1998 | Bartel | |
| 5,762,867 A | 6/1998 | D'Silva | |
| 5,800,478 A | 9/1998 | Chen et al. | |
| 5,803,729 A | 9/1998 | Tsimerman | |
| 5,857,767 A | 1/1999 | Hochstein | |
| 5,873,645 A | 2/1999 | Belfer | |
| 5,912,470 A | 6/1999 | Eibofner et al. | |
| 5,928,220 A | 7/1999 | Shimoji | |
| 5,949,805 A | 9/1999 | Mordaunt et al. | |
| 5,967,653 A | 10/1999 | Miller et al. | |
| 5,975,895 A | 11/1999 | Sullivan | |
| 6,008,264 A | 12/1999 | Ostler et al. | |
| 6,033,223 A | 3/2000 | Narusawa et al. | |
| 6,045,240 A | 4/2000 | Hochstein | |
| 6,046,460 A | 4/2000 | Mertins | |
| 6,065,965 A | 5/2000 | Rechmann | |
| 6,068,474 A | 5/2000 | Senn et al. | |
| 6,077,073 A | 6/2000 | Jacob | |
| 6,086,367 A | 7/2000 | Levy | |
| 6,095,812 A | 8/2000 | Senn et al. | |
| 6,102,696 A | 8/2000 | Osterwalder et al. | |
| 6,113,212 A | 9/2000 | Ng | |
| 6,123,545 A | 9/2000 | Eggler et al. | |
| 6,155,823 A | 12/2000 | Nagel | |
| 6,159,005 A | 12/2000 | Herold et al. | |
| 6,161,937 A | 12/2000 | Rosenstatter | |
| 6,168,431 B1 | 1/2001 | Narusawa et al. | |
| 6,171,105 B1 | 1/2001 | Sarmadi | |
| 6,171,331 B1 | 1/2001 | Bagraev et al. | |
| 6,186,786 B1 | 2/2001 | Trushkowsky | |
| 6,193,510 B1 | 2/2001 | Tsimerman | |
| 6,200,134 B1 | 3/2001 | Kovac et al. | |
| 6,208,788 B1 | 3/2001 | Nosov | |
| 6,220,722 B1 | 4/2001 | Begemann | |
| 6,280,187 B1 | 8/2001 | Slone | |
| 6,280,188 B1 | 8/2001 | Ross | |
| 6,285,476 B1 | 9/2001 | Carlson et al. | |
| 6,331,111 B1 | 12/2001 | Cao | |
| 6,345,982 B1 | 2/2002 | Meyer | |
| 6,350,041 B1 | 2/2002 | Tarsa et al. | |
| 6,371,636 B1 | 4/2002 | Wesson | |
| 6,379,149 B1 | 4/2002 | Franetzki | |
| 6,398,383 B1 | 6/2002 | Huang | |

| | | |
|---|---|---|
| 6,402,347 B1 | 6/2002 | Maas et al. |
| 6,419,483 B1 | 7/2002 | Adam et al. |
| 6,439,888 B1 | 8/2002 | Boutoussov et al. |
| 6,468,077 B1 | 10/2002 | Melikechi et al. |
| 6,492,725 B1 | 12/2002 | Loh et al. |
| 6,511,317 B2 | 1/2003 | Melikechi et al. |
| 6,523,959 B2 | 2/2003 | Lee et al. |
| 6,535,533 B2 | 3/2003 | Lorenzen et al. |
| 6,558,829 B1 | 5/2003 | Faris et al. |
| 6,591,898 B1 | 7/2003 | Chu et al. |
| 6,638,063 B2 | 10/2003 | Otsuka |
| 6,676,306 B2 | 1/2004 | Ikeda et al. |
| 6,683,421 B1 | 1/2004 | Kennedy et al. |
| 6,692,250 B1 | 2/2004 | Decaudin et al. |
| 6,692,251 B1 | 2/2004 | Logan et al. |
| 6,692,252 B2 | 2/2004 | Scott |
| 6,695,614 B2 | 2/2004 | Plank |
| 6,702,576 B2 | 3/2004 | Fischer et al. |
| 6,709,128 B2 | 3/2004 | Gordon et al. |
| 6,712,576 B2 | 3/2004 | Skarzenski et al. |
| 6,719,558 B2 | 4/2004 | Cao |
| 6,719,559 B2 | 4/2004 | Cao |
| 6,737,681 B2 | 5/2004 | Koda |
| 6,755,647 B2 | 6/2004 | Melikechi et al. |
| 6,755,648 B2 | 6/2004 | Cao |
| 6,755,649 B2 | 6/2004 | Cao |
| 6,780,010 B2 | 8/2004 | Cao |
| 6,783,362 B2 | 8/2004 | Cao |
| 6,799,967 B2 | 10/2004 | Cao |
| 6,824,294 B2 | 11/2004 | Cao |
| 6,827,468 B2 | 12/2004 | Galli |
| 6,876,681 B2 | 4/2005 | Nagamatsu |
| 6,910,886 B2 | 6/2005 | Cao |
| 6,918,762 B2 | 7/2005 | Gill et al. |
| 6,926,524 B2 | 8/2005 | Cao |
| 6,929,472 B2 | 8/2005 | Cao |
| 6,932,599 B1 | 8/2005 | Hartung |
| 6,932,600 B2 | 8/2005 | Cao |
| 6,953,340 B2 | 10/2005 | Cao |
| 6,955,537 B2 | 10/2005 | Cao |
| 6,969,180 B2 | 11/2005 | Waters |
| 6,969,253 B2 | 11/2005 | Cao |
| 6,971,875 B2 | 12/2005 | Cao |
| 6,971,876 B2 | 12/2005 | Cao |
| 6,974,319 B2 | 12/2005 | Cao |
| 6,979,193 B2 | 12/2005 | Cao |
| 6,979,194 B2 | 12/2005 | Cao |
| 6,981,867 B2 | 1/2006 | Cao |
| 6,986,782 B2 | 1/2006 | Chen et al. |
| 6,988,890 B2 | 1/2006 | Cao |
| 6,988,891 B2 | 1/2006 | Cao |
| 6,991,356 B2 | 1/2006 | Tsimerman et al. |
| 6,991,456 B2 | 1/2006 | Plank |
| 6,994,546 B2 | 2/2006 | Fischer et al. |
| 7,001,057 B2 | 2/2006 | Plank et al. |
| 7,033,381 B1 | 4/2006 | Larsen |
| 7,066,733 B2 | 6/2006 | Logan et al. |
| 7,079,391 B2 | 7/2006 | Wellhofer |
| 7,135,034 B2 | 11/2006 | Friedman et al. |
| 7,198,386 B2 | 4/2007 | Zampini et al. |
| 7,225,859 B2 | 6/2007 | Mochizuki et al. |
| 7,434,964 B1 | 10/2008 | Zheng et al. |
| 7,494,248 B2 | 2/2009 | Li |
| 7,568,817 B2 | 8/2009 | Lee et al. |
| 7,645,056 B1 | 1/2010 | Mills et al. |
| 2001/0007739 A1 | 7/2001 | Eibofner et al. |
| 2001/0046652 A1 | 11/2001 | Ostler et al. |
| 2002/0014864 A1 | 2/2002 | Gemunder et al. |
| 2002/0048295 A1 | 4/2002 | Kato et al. |
| 2002/0051367 A1 | 5/2002 | Hooker et al. |
| 2002/0054615 A1 | 5/2002 | Nagamatsu et al. |
| 2002/0115037 A1 | 8/2002 | Cao |
| 2002/0133970 A1 | 9/2002 | Gordon et al. |
| 2002/0151941 A1 | 10/2002 | Okawa et al. |
| 2002/0172914 A1 | 11/2002 | Cao |
| 2002/0172918 A1 | 11/2002 | Burtscher et al. |
| 2002/0177096 A1 | 11/2002 | Cao |
| 2002/0181947 A1 | 12/2002 | Cao |
| 2002/0187454 A1 | 12/2002 | Melikechi et al. |
| 2003/0000213 A1 | 1/2003 | Christensen et al. |
| 2003/0015667 A1 | 1/2003 | MacDougald et al. |
| 2003/0021310 A1 | 1/2003 | Harding |
| 2003/0036031 A1 | 2/2003 | Lieb et al. |
| 2003/0048608 A1 | 3/2003 | Crocker et al. |
| 2003/0218880 A1 | 11/2003 | Brukilacchio |
| 2003/0219693 A1 | 11/2003 | Cao |
| 2004/0005524 A1 | 1/2004 | Oxman et al. |
| 2004/0026706 A1 | 2/2004 | Bogner et al. |
| 2004/0029069 A1 | 2/2004 | Gill et al. |
| 2004/0032728 A1 | 2/2004 | Galli |
| 2004/0043351 A1 | 3/2004 | Logan et al. |
| 2004/0054386 A1 | 3/2004 | Martin et al. |
| 2004/0070990 A1 | 4/2004 | Szypszak |
| 2004/0090794 A1 | 5/2004 | Ollett et al. |
| 2004/0120148 A1 | 6/2004 | Morris et al. |
| 2004/0185413 A1 | 9/2004 | Gill et al. |
| 2004/0213016 A1 | 10/2004 | Rice |
| 2005/0003322 A1 | 1/2005 | Logan et al. |
| 2005/0077865 A1 | 4/2005 | Durbin et al. |
| 2005/0082989 A1 | 4/2005 | Jones et al. |
| 2005/0093506 A1 | 5/2005 | Hamada et al. |
| 2005/0096661 A1 | 5/2005 | Farrow et al. |
| 2005/0099824 A1 | 5/2005 | Dowling et al. |
| 2005/0116176 A1 | 6/2005 | Aguirre et al. |
| 2005/0142514 A1 | 6/2005 | Scott |
| 2005/0158687 A1 | 7/2005 | Dahm |
| 2005/0171408 A1 | 8/2005 | Parker |
| 2005/0196721 A1 | 9/2005 | Jackson et al. |
| 2005/0231983 A1 | 10/2005 | Dahm |
| 2005/0236586 A1 | 10/2005 | Hartung |
| 2005/0244993 A1 | 11/2005 | Bogner et al. |
| 2006/0001384 A1 | 1/2006 | Tain et al. |
| 2006/0024638 A1 | 2/2006 | Rosenblood et al. |
| 2006/0092639 A1 | 5/2006 | Livesay et al. |
| 2006/0102917 A1 | 5/2006 | Oyama et al. |
| 2006/0188836 A1 | 8/2006 | Logan et al. |
| 2007/0123957 A1 | 5/2007 | Friedman et al. |
| 2007/0279862 A1 | 12/2007 | Li |
| 2008/0007954 A1 | 1/2008 | Li |
| 2008/0007955 A1 | 1/2008 | Li |
| 2008/0205062 A1 | 8/2008 | Dahm et al. |
| 2008/0278954 A1 | 11/2008 | Speier |

FOREIGN PATENT DOCUMENTS

| | | |
|---|---|---|
| DE | 42 11 233 A1 | 8/1993 |
| DE | 29511927 U1 | 2/1997 |
| DE | 10010638 A1 | 3/2000 |
| EP | 0116405 A1 | 8/1984 |
| EP | 0166405 A1 | 8/1984 |
| EP | 0 191 500 | 8/1986 |
| EP | 0266038 B1 | 10/1991 |
| EP | 0320080 B1 | 8/1993 |
| EP | 0672435 A1 | 9/1995 |
| EP | 0678282 A2 | 10/1995 |
| EP | 709698 | 5/1996 |
| EP | 0755662 A1 | 1/1997 |
| EP | 0780103 A2 | 6/1997 |
| EP | 0 830 850 A1 | 3/1998 |
| EP | 0 830 851 B1 | 3/1998 |
| EP | 0 830 852 B1 | 3/1998 |
| EP | 0879582 A2 | 11/1998 |
| EP | 0568666 B1 | 11/1999 |
| EP | 1 031 326 A1 | 8/2000 |
| EP | 1 090 607 A1 | 4/2001 |
| EP | 1 090 608 A1 | 4/2001 |
| EP | 1 112 721 A1 | 7/2001 |
| EP | 1 138 276 A1 | 10/2001 |
| EP | 1 206 923 A1 | 5/2002 |
| EP | 1 253 547 A2 | 10/2002 |
| EP | 0 740 567 B1 | 11/2002 |
| EP | 0 959 803 B1 | 5/2003 |
| EP | 1 309 048 A1 | 5/2003 |
| EP | 0 884 025 B1 | 7/2003 |
| EP | 0 885 025 B1 | 11/2003 |
| EP | 1 374 797 A1 | 1/2004 |
| EP | 1 388 326 A2 | 2/2004 |
| EP | 1 103 232 B1 | 9/2004 |
| EP | 1 138 349 B1 | 9/2004 |

| | | | |
|---|---|---|---|
| EP | 0 736 307 B1 | 10/2004 |
| EP | 0 780 101 B1 | 10/2004 |
| EP | 0 998 880 B1 | 4/2005 |
| EP | 1 093 765 B1 | 5/2005 |
| EP | 1 228 738 B1 | 3/2006 |
| EP | 0 880 945 B1 | 4/2006 |
| GB | 2212010 A | 7/1989 |
| GB | 2218636 A | 11/1989 |
| GB | 2329756 A | 3/1999 |
| GB | 2 385 137 A | 8/2003 |
| GB | 2 385 429 A | 8/2003 |
| JP | 51-42607 | 4/1976 |
| JP | 58-033859 | 2/1983 |
| JP | 61-158980 | 8/1986 |
| JP | 62-0066957 | 3/1987 |
| JP | 63-271983 | 11/1988 |
| JP | 04-066957 | 3/1992 |
| JP | 06-030275 A | 2/1994 |
| JP | 6285508 A | 10/1994 |
| JP | 7163863 A | 6/1995 |
| JP | 07-240536 | 9/1995 |
| JP | 8-116093 | 5/1996 |
| JP | 08-116093 | 5/1996 |
| JP | 8141001 A | 6/1996 |
| JP | 09-010238 | 1/1997 |
| JP | 8194786 A | 7/1997 |
| JP | 10-027926 A | 1/1998 |
| JP | 10-033573 A | 2/1998 |
| JP | 2000-031546 A | 1/2000 |
| JP | 2002-084029 A | 3/2002 |
| JP | 2002-111116 A | 4/2002 |
| JP | 2002-335019 A | 11/2002 |
| WO | 83/01311 A1 | 4/1983 |
| WO | 84/04463 A1 | 11/1984 |
| WO | 92/02275 A1 | 2/1992 |
| WO | 93/09847 A1 | 5/1993 |
| WO | 93/21842 A1 | 11/1993 |
| WO | 95/07731 A1 | 3/1995 |
| WO | 95/19810 A1 | 7/1995 |
| WO | 95/26217 A1 | 10/1995 |
| WO | 97/36552 A1 | 10/1997 |
| WO | 97/37722 A1 | 10/1997 |
| WO | 97/46279 A1 | 12/1997 |
| WO | 97/46280 A1 | 12/1997 |
| WO | 98/03131 A1 | 1/1998 |
| WO | 98/04317 A1 | 2/1998 |
| WO | 99/09071 A1 | 2/1999 |
| WO | 99/11324 A1 | 3/1999 |
| WO | 99/16136 A1 | 4/1999 |
| WO | 99/20346 A1 | 4/1999 |
| WO | 99/35995 A1 | 7/1999 |
| WO | 00/01464 A2 | 1/2000 |
| WO | 00/02491 A1 | 1/2000 |
| WO | 00/13608 A1 | 3/2000 |
| WO | 00/15296 A1 | 3/2000 |
| WO | 00/41726 A2 | 7/2000 |
| WO | 00/41767 A1 | 7/2000 |
| WO | 00/41768 A1 | 7/2000 |
| WO | 00/43067 A1 | 7/2000 |
| WO | 00/43068 A1 | 7/2000 |
| WO | 00/43069 A1 | 7/2000 |
| WO | 00/45733 A1 | 8/2000 |
| WO | 00/67048 A2 | 11/2000 |
| WO | 00/67660 A1 | 11/2000 |
| WO | 01/01118 A1 | 1/2001 |
| WO | 01/03770 A1 | 1/2001 |
| WO | 01/14012 A1 | 3/2001 |
| WO | 01/19280 A1 | 3/2001 |
| WO | 01/24724 A1 | 4/2001 |
| WO | 01/54770 A1 | 8/2001 |
| WO | 01/60280 A1 | 8/2001 |
| WO | 01/64129 A1 | 9/2001 |
| WO | 01/65613 A1 | 9/2001 |
| WO | 01/68035 A2 | 9/2001 |
| WO | 01/69691 A1 | 9/2001 |
| WO | 02/06723 A1 | 1/2002 |
| WO | 02/09610 A1 | 2/2002 |
| WO | 02/11640 A2 | 2/2002 |
| WO | 02/13231 A2 | 2/2002 |
| WO | 02/32505 A1 | 4/2002 |
| WO | 02/33312 A2 | 4/2002 |
| WO | 02/49721 A1 | 6/2002 |
| WO | 02/051327 A1 | 7/2002 |
| WO | 02/56787 A2 | 7/2002 |
| WO | 02/060723 A2 | 8/2002 |
| WO | 02/69839 A1 | 9/2002 |
| WO | 02/80808 A1 | 10/2002 |
| WO | 02/097501 A1 | 12/2002 |
| WO | 03/096387 A2 | 11/2003 |
| WO | 03/096925 A1 | 11/2003 |
| WO | 03/107440 A2 | 12/2003 |
| WO | 2006/001928 A1 | 1/2006 |
| WO | 2006/014363 A2 | 2/2006 |

OTHER PUBLICATIONS

LumiLeds Lighting LLC, "Application Brief AB20-5, replaces AN1149-5, Secondary Optics Design Considerations for Super Flux LEDs," Copyright © 2002 LumiLeds Lighting, Publication No. AB20-5.

Burgess, John et al., "An Evaluation of Four Light-curing Units Comparing Soft and Hard Curing," Pract. Periodont. Aesthet. Dent. 11(1), 125-132, 1999.

Feltzer A.J., et al., "Influence of Light Intensity on Polymerization Shrinkage and Integrity of Restoration-cavity Interface," Eur. J. Oral Sciences, 103, 322-326, 1995.

Kanca, III, John et al., "Pulse Activation: Reducing Resin-Based Composite Contraction Stresses at teh Enamel Cavosurface Margins," Am. J. of Dentistry, 12(3), 107-112, 1999.

Kato, Hiromasa, "Relationship Between the Velocity of Polymerization and Adaption to Dentin Cavity Wall of Light-Cured Composite," Dental Materials J. 6(1), 32-37, 1987.

Koran, Peter et al., "Effect of Sequential Versus Continuous Irradiation of a Light-Cured Resin Composite on Shrinkgge, Viscosity, Adhesion, and Degree of Polymerization," Am. J. of Dentistry, 11, No. 1, 17-22, 1998.

Mayes, Joe H., "Curing Lights; An Overview," Ormvo, vol. 9, No. 2, 2000, p. 15-17.

Mehl, A. et al., "Physical Properties and Gap Formation of Light-Cured Composites With and Without 'Softstart-Polymerization,'" J of Dentistry, 25, 321-330, 1997.

Sakaguchi, Ronald L., et al., "Reduced Light Energy Density Decreases Post-Gel Contraction While Maintaining Degree of Conversion in Composites," J. of Dentistry, 26, 695-700, 1998.

Schlager, Kenneth J., et al., "An LED-Array Light Source for Medical Therapy," SPIE vol. 1892, Medical Lasers and Systems II, p. 26-35, 1993.

Swift Jr., Edward, et al. "Contemporary Photocuring Issues, Part II," J. Esthetic Dentistry, 12(1), 50-57, 2000.

Tarle, Z. et al., "The Effect of the Photopolymerization Method on the Quality of Composite Resin Samples," J. or Oral Rehab, 25, 436-442, 1998.

* cited by examiner

OPTICAL IRRADIATION DEVICE

RELATED APPLICATIONS

This application is a divisional of U.S. patent application Ser. No. 09/509,433 filed May 30, 2000, entitled "OPTICAL IRRADIATION DEVICE HAVING LED AND HEAT PIPE"; which application is a 371 of PCT/GB98/02905 filed Sep. 25, 1998, entitled "OPTICAL IRRADIATION DEVICE" and claims the benefit of priority to United Kingdom Patent Application Serial No. 9720443.2 filed Sep. 25, 1997, entitled "DENTAL CURING" and United Kingdom Patent Application Serial No. 9806046.0 filed Mar. 20, 1998, entitled "DENTAL CURING." These prior applications are incorporated herein by reference in their entirety.

TECHNICAL FIELD

This invention relates to an optical irradiation device, especially a compact portable irradiation device suitable for use as a light polymerisation source.

It has already been proposed to use light-emitting diodes LEDs in a hand held device to produce a focused beam of light to cure dental materials. Blue light at a peak wavelength of about 470 nm is used to harden dental polymers which contain camphoroquinone as the photoinitator in a methacrylate polymerisation process. However, there is a problem in producing a sufficient level of irradiance even with a clustered array of LEDs, to cure the known dental polymers in the recommended time. At the lower levels of irradiance available generally below 300 mW/sq. cm, longer curing times have to be allowed, which reduces the efficiency of the dental treatment delivered.

DISCLOSURE OF THE INVENTION

An object of the present invention is to provide an optical irradiation device that employs LEDs, and thereby has the benefits of compactness, portability, ruggedness and long life, but which also produces improved levels of irradiance at and above 300 mW/sq. cm.

According to a first aspect of the invention, LEDs are clustered in an irradiation device by forming shaped facets on adjacent LEDs which allow them to adjoin more closely than they would otherwise with conventional spherical outer surfaces as manufactured currently.

According to a second aspect, the invention consists in a tapered light guide for an optical irradiation device, which light guide is tapered from its input end to its output end and has an intermediate region of minimum diameter in which a bend is formed.

According to a third aspect, the invention consists in an optical irradiation device employing LEDs and incorporating a heat pipe to cool the LEDs.

According to a fourth aspect, the invention consists in a heat pipe comprising inner and outer walls that extend longitudinally from one end of the heat pipe to the other and define an annular space therebetween containing a material that serves to absorb heat by a phase change, the annular space being divided by internal walls into a plurality of fluid flow channels that extend longitudinally between said ends, some of said channels being adapted to conduct the liquid/vapour phase of said material from the hot end of the heat pipe to the cold end, and other channels being adapted to return said liquid phase from the cold end of the pipe to the hot end.

According to a fifth aspect, the invention consists in an irradiation device employing LEDs and a tapered light guide to collect radiation emitted by the LEDs and deliver this to an output beam, wherein two or more tapered light guides are arranged in series so that successive guides receive radiation from preceding guides, and a group of LEDs is provided at the input end of each guide, each successive guide preferably being provided with a ring of LEDs around the output end of the preceding guide.

The first aspect of the invention means that LEDs occupy more of the available space, and a fixed number produce a higher radiant intensity. Thus, smaller numbers of LEDs can be used to produce a desired level of irradiance, which in turn reduces the power required to drive the device and the heat generated by it. Furthermore, the device can be made more compact. Packing of the LEDs in this way may involve a slight reduction in the output of each LED, but the more effective packing density produces an overall increase in irradiance.

Typically, a central LED might have a polygonal outer surface, and a first ring of LEDs would be arranged around it, each with a flat face to abut a corresponding face of the central LED and possibly each having a pair of radiating side faces which abut adjacent LEDs in the first ring. Furthermore, a second or more rings of LEDs could be arranged concentrically with the first ring, each with respective adjacent flat side faces abutting one another and possibly with inwardly diverted faces abutting respective outwardly directed faces of the LEDs of the inner ring. Alternatively, a single ring or two or more concentric rings of LEDs could be used without a central LED.

DESCRIPTION OF THE DRAWINGS

The invention will now be described by way of example with reference to the accompanying drawings, in which.

MODE OF CARRYING OUT THE INVENTION

Figure 1:
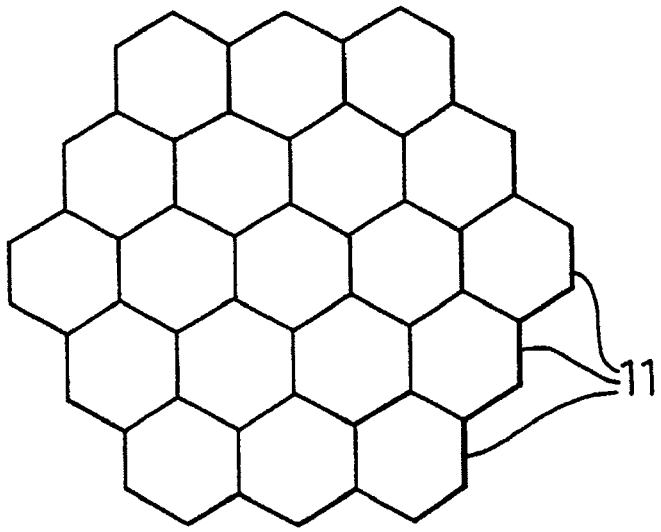
FIG. 1 is a schematic cross-section through a first embodiment of the invention comprising a cluster of hexagonal section LEDs.

In a typical optical irradiation device according to the invention, a plurality of LEDs are clustered together so as to direct emitted radiation into a single beam. A cluster of LEDs 43 is shown in side view in FIG. 4, and in plan view or cross-section in FIGS. 1 to 3. Each LED comprises a light-emitting semiconductor Pn junction (not shown) which is encapsulated in an outer plastics envelope, the profile of which is shown in the drawings. The sides of the LED envelope are shaped to allow the LEDs to be clustered together more closely at their bases, thereby increasing the ratio of occupied to unoccupied space in the cluster of LEDs. The tips of the LEDs are substantially spherical and transmit the radiation to form the beam.

In the embodiment of the invention illustrated in FIG. 1 the outer envelope of the LEDs is hexagonal in cross-section, and the LEDs are clustered in the manner of a honeycomb as shown, with adjacent facets abutting one another.

Figure 2:
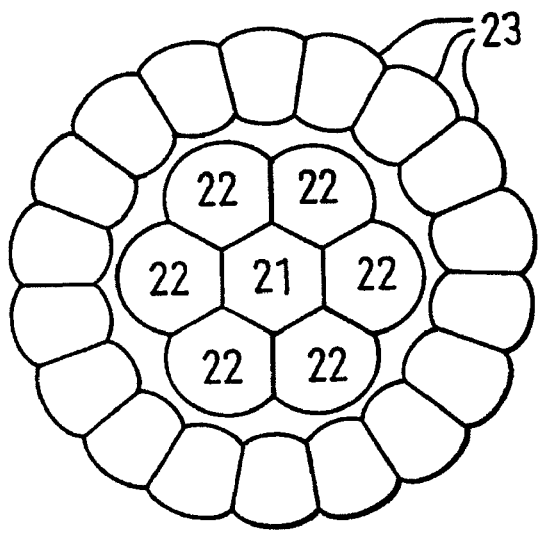
FIG. 2 is a schematic cross-section through a second embodiment of the invention comprising a cluster of an inner group of LEDs and an outer ring of LEDs.

In the second embodiment of the invention illustrated in FIG. 2, a central LED 21 of hexagonal cross-section has facets which abut adjacent facets of six LEDs 22 in a first ring of LEDs with radially extending side facets that allow adjacent LEDs in the ring to abut one another. A second ring of LEDs 23 is arranged around the first ring of LEDs, and these LEDs 23 have radially extending side facets that allow adjacent LEDs in the ring to abut one another.

Figure 3:
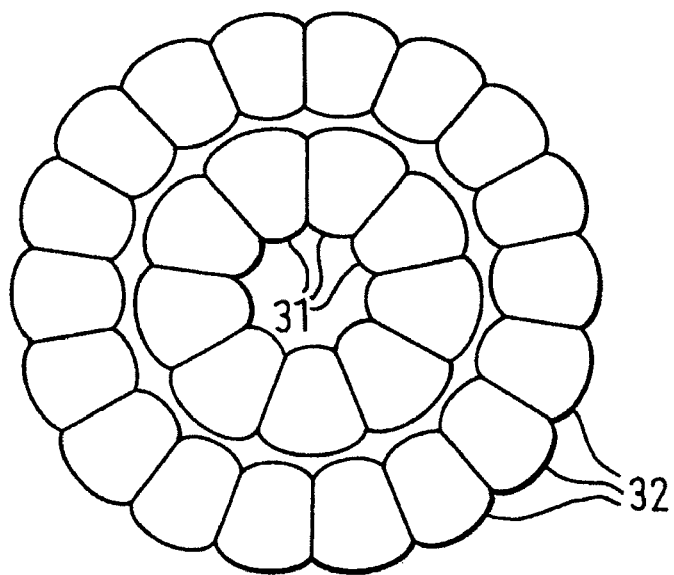
FIG. 3 is a schematic cross-section through a third embodiment of the invention comprising a cluster of two rings of LEDs.

In a third embodiment of the invention shown in FIG. 3, an inner ring of nine LEDs 31 in a first ring is contained within a second ring of LEDs 32, and radially extending side facets of the LEDs in both rings allow adjacent LEDs in each ring to abut one another.

Both the second embodiment of FIG. 2 and the third embodiment of FIG. 3 may be modified by the addition of one or more further concentric rings of LEDs. Also, the circumferential facets of the LEDs of each ring may be shaped to abut similarly shaped circumferential facets of the adjacent ring of LEDs.

In yet another embodiment, the central group of LEDs 21,22 of FIG. 2 may be replaced by the same number of LEDs in a honeycomb cluster. Yet another embodiment may consist of the single ring of LEDs 31 shown in FIG. 3. It will be appreciated in all three illustrated embodiments, the LEDs are mounted in a substantially flat plane.

In modifying the conventional optical sphere shape of the outer plastics envelope of a LED care has to be taken to preserve as much as possible of the focusing effect of the envelope to maximise the total irradiance. However, because the envelope of existing LEDs have a tapered shape to assist their removal from the mould during manufacture, the shaped side facets can be formed around the broader base of the LED to change its cross-section, for example to become hexagonal, but with these facets having a reducing effect on the shape of the envelope towards its tip where the focusing effect of the envelope is concentrated. Thus the invention can employ existing LEDs and modify their shape in a secondary manufacturing process, for example, using jigs, or the invention can employ LEDs which have been specially manufactured with the required outer envelope shape to accommodate better clustering.

The shaped facets of the LEDs may be polished to enhance reflection and help reduce any loss of optical powers. Additionally, a reflective metallic film may be applied to the shaped facets to further enhance reflection.

The LEDs may also incorporate a microlens or microlens array to aid collimation of the beam.

The electrical connections of the LEDs, known as lead frames 44, are connected to respective positive and negative power terminals or bus bars 42. Preferably, these terminals are adapted to serve the dual function of heat sinks to help remove heat generated by the LEDs 43. Thus, the terminals are formed of a good thermal conductor such as copper, and are located in the optimum location relative to the LEDs and the external surfaces of the device. In one particular embodiment most suited to the LED array of FIG. 3, the terminals 42 take the form of two concentric rings, each lying adjacent to the bases of one ring of LEDs 31 or 32. Preferably, the negative terminal is the outer one because the lead frames 44 to the negative terminal of the LEDs generally get hotter than the lead frames 44 to the positive terminal of the LEDs.

Figure 4:
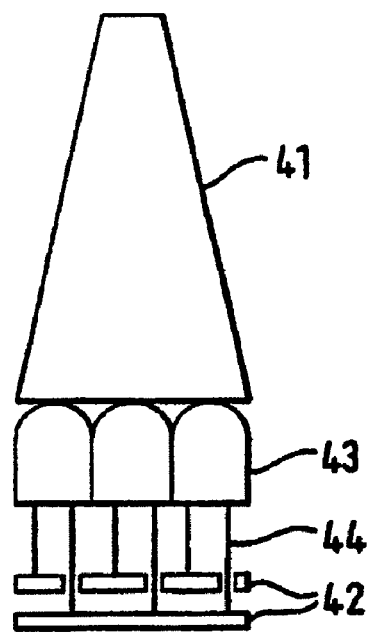
FIG. 4 is a schematic side elevation of a fourth embodiment of the invention.

The typical optical irradiation device according to the invention also preferably incorporates a tapered light guide, shown as guide 41 in FIG. 4, to collect light emitted by the LEDs and deliver this as an output beam. It is known to use light guides with adiabatic optical tapers in optical irradiation devices so that there is total internal reflection of the light as it is conducted from the light source to the output. However, an advantage of the invention is that the more compact cross-section of the LED cluster means that the diameter at the input end of the light guide can be smaller, and thus a smaller angle of adiabatic taper (i.e. the ratio of the diameter of the input end to the output end of the light guide) can be provided in the light guide with the consequent more efficient transmission of radiant energy and increased illuminance. This improvement is most marked compared with a conventional approach of simply increasing the numbers of LEDs in a cluster at ever increasing diameters with decreasing beneficial effect on illuminance and increasing detrimental effect on compactness, heat generation and cost.

Figure 6:
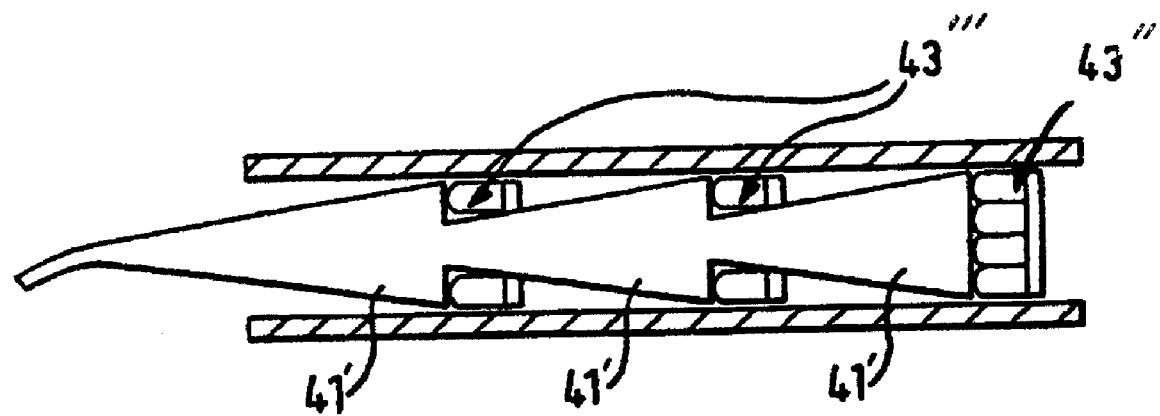
FIG. 6 is a schematic longitudinal section through a sixth embodiment of the invention.

In another embodiment of the invention, illustrated in FIG. 6, two or more adiabatic tapered light guides 41' are arranged in series, each with a corresponding cluster of LEDs 43", 43''', but with successive clusters forming a ring around the end of one light guide as it connects to the next. Alternatively, each successive ring of LEDs 43''' may be replaced by just one or a fewer number of LEDs. This arrangement allows the overall diameter of the device to be kept relatively small as the LED clusters 43", 43''' are arranged in groups along the length of the device.

Figure 5:
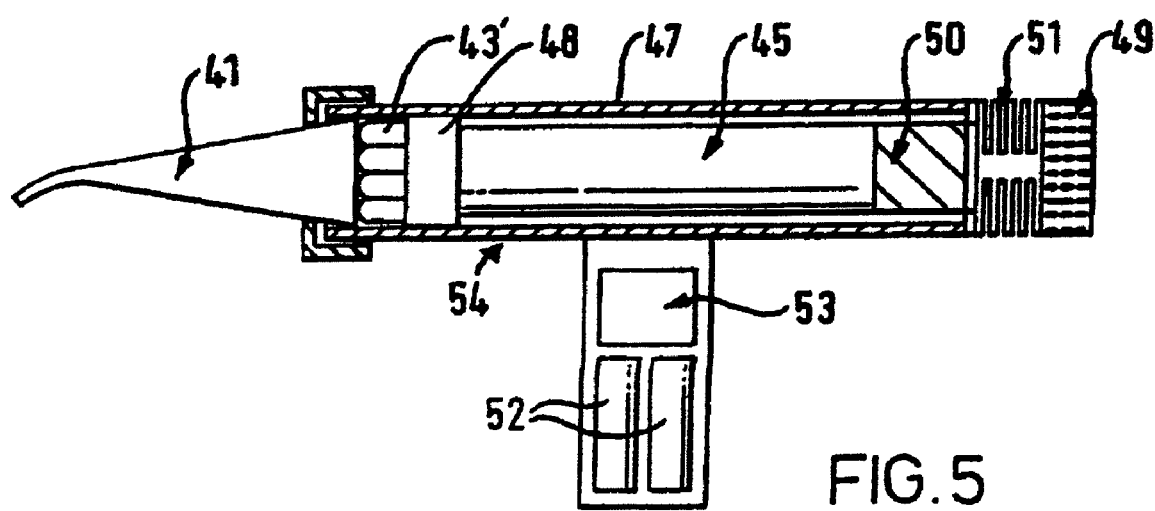
FIG. 5 is a schematic longitudinal section through a fifth embodiment of the invention.

In the preferred embodiment of FIG. 4, a single tapered light guide 41 is provided. If required, the light guide can be curved along its length, as shown in FIG. 5, to direct the output beam to suit a particular application, this being a known practice with existing light guides. The light guide may be machined from cast acrylic plastic and bent, or could be made from glass or other optically transparent materials.

Figure 8:
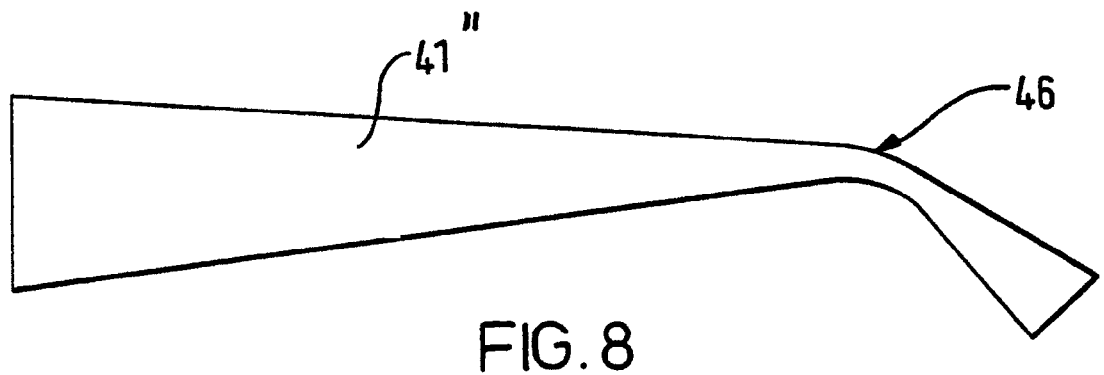
FIG. 8 is a schematic side elevation of a tapered light-guide according to another embodiment of the invention.

An alternative light guide is illustrated in FIG. 8 in which the bend in the light guide 41 is provided at a waisted section 46 in its length which reduces to a minimum diameter before widening again to a larger diameter towards its output end. By forming the bend at the minimum diameter, the light transmission losses of the light guide caused by the bend are reduced, but the effective cross-sectional area of the output beam is maintained at the required level.

Fused fibre-bundle light guides have the advantage of individual fibres being of a relatively small diameter so that they can be bent over a tighter radius without the greater losses associated with larger diameter fibres when bent over the same radius. However, conventional fused-fibre bundles have the disadvantage of a packing fraction loss, that is, the outer cladding of the fibre uses up a significant proportion of the cross-section of the light guide into which light from the semiconductor array is directed, thus reducing the amount of transmitted radiation available from the semiconductor source. Preferably, therefore, in one embodiment of the invention, illustrated in FIG. 7, the guide comprises a few shaped fibres 61, 61' placed adjacent to each other and fused together.

A guide of this design is manufactured by MicroQuartz Sciences Inc. of Phoenix, Ariz., USA. In this way, the diameter of each fibre is smaller than a single homogeneous guide rod so that they allow greater light transmission on bending around the same bend radius, but also the packing fraction is also greatly reduced over conventional fibre guides, resulting in a greater than 90% core availability at the input end of the guide.

In another embodiment of the invention, a graded-index optical light guide is used. A graded-index light guide has no sudden interface between the cladding and the core. Instead, the refractive index varies either radially or axially. In one embodiment, the gradient of the refractive index of the light guide varies both radially and axially so that the light energy is favourably manipulated. A guide that uses a stepped index could also be used with the same axial and radial variation in refractive index. In this way, the numeric aperture can be varied at either end of the guide to achieve the desired transmission.

Figure 7:
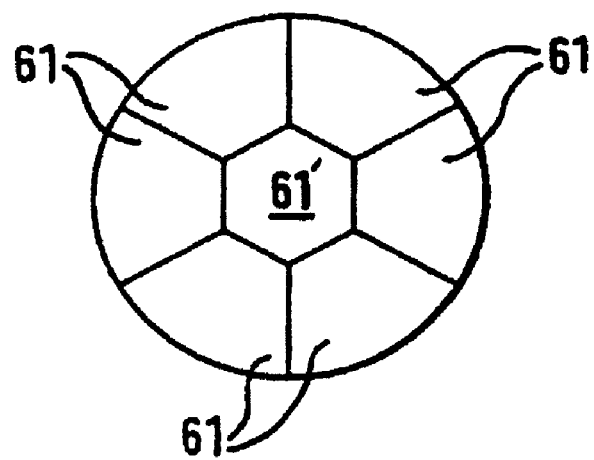
FIG. 7 is a schematic cross-section through a bundle of light guide fibres with modified sections.

In other embodiments of the invention, instead of providing a single tapered light guide, each LED or groups of LEDs could be provided with its own light guide fibre incorporating an adiabatic optical taper, and the output ends of these fibres could be collected together to form a single output beam. The input end of the fibre would be moulded optically to the adjacent LED or group of LEDs for efficient transmission of radiation. In this way, the diodes can be spaced more widely to dissipate unwanted heat. In yet another embodiment of the invention, each LED could be adjusted so that its outer envelope is extended into a fibre light guide which incorporates an adiabatic optical taper. In yet another embodiment, the section of the fibres may be modified so that shaped faces of the fibres fit together to reduce the interstitial space. One embodiment of this design could be as shown in FIG. 7.

The light guide or light guides used according to the invention may be formed with an outer metallic coating to improve its performance.

It will be appreciated that the irradiance of the device according to the invention can be varied by varying the input power, number of LEDs, or by varying the adiabatic taper of the light guide.

Cooling of the LED cluster can be aided according to another feature of the invention by arranging that the electrical connections of each LED are thermally connected to one or more heat pipes. Conventional LED irradiation devices usually include a heat sink to conduct away the heat from the LED chips. Heat sinks are generally slow and inefficient in conducting heat away from a heat source compared with heat pipes. Heat pipes conduct heat away rapidly by using the latent heat of a substance, such as water, which is vaporized by the heat from the source. The vapour moves at high speed to the cooler end of the heat pipe and condenses. Heat pipes are unique in their ability to conduct heat rapidly in this way.

FIG. 5 shows a device according to the invention which incorporates a light guide 41 and cluster of LEDs 43 as shown in FIG. 4 together with a heat pipe 45 as a single lumen in the main body 46 of the device. The hotter of the LED leads is preferably placed nearer the heat pipe 45 or outer case 47 of the LED cluster so that the heat path of the hotter lead is shorter. A thermal connector 48 may be provided between the LEDs 43' and the end of the heat pipe 45. If required, additional forced cooling means may be used for example, a fan 49 or Peltier device 50 in juxtaposition to the pipe. In addition, a heat sink 51 may be provided.

Because of the greater cooling ability of heat pipes, they allow the LEDs to be driven in such a manner as to produce more radiation, and thus allows a more powerful device to be manufactured.

Figure 9:
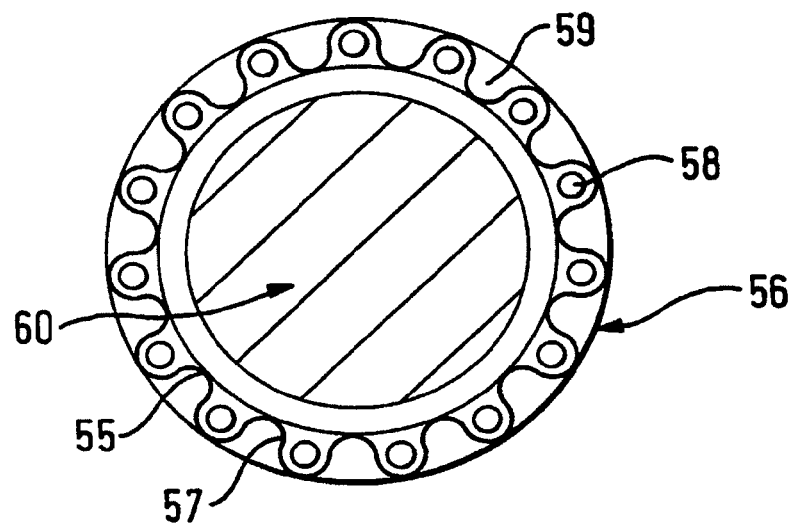
FIG. 9 is a schematic cross-section through a heat pipe according to the invention.

For portable use, the LEDs are operated from batteries 52, which are located in a hand grip 53 attached to the body 46, in FIG. 5. However, the heat pipe design can be modified as shown in FIG. 9 to accommodate batteries. The heat pipe consists of two concentric heat conducting tubes 55,56 with a folded interstitial heat conduction element 57 between these tubes similar in appearance to a length of corrugated sheet rolled into a tube. This lies within the concentric tubes. The wicks 58 of the heat pipe can then be placed in alternative grooves in the corrugated sheet, which the empty grooves 59 allow for the rapid movement of the vapour formed at the warmer end of the heat pipe.

By designing the heat pipe in this way batteries, capacitors, supercapacitors or other energy source 60 can be located within the inner wall 55 of the heat pipe.

In some embodiments, for example, where there are a large number of LEDs, a heat sink 51 may be necessary in addition to the heat pipe 45. The intermittent use of an LED irradiation device for dental curing, means that with careful design, a heat sink may be omitted. If cooling to below the ambient temperature is required, such as may be the case in extreme environments, a Peltier device 50 may be added to the heat pipe, although a Peltier device will result in a greater consumption of power and a requirement for greater heat dissipation.

The wavelengths of the LED used will depend upon the applications of the device. A LED emitting blue light with a peak wavelength of about 470 mm is used to harden dental polymers, but a LED emitting red light may be useful for photodynamic therapy, for example, cancer therapy.

The wavelength of light emitted by the LEDs may be modified in a light guide by doping the material from which it is composed with fluorescent material. This can serve to lengthen the wavelength of the emitted light so as to suit the particular application.

The choice of LED is also important in terms of its construction, diameter, irradiance and light angular spread pattern. From a range of known LEDs the best available choice has been determined as that with a 3 mm diameter rather than a 5 mm diameter and an angular spread of 30 degrees rather than 15 or 45 degrees. Nichia is the manufacturer of these LEDs.

It will be appreciated that the term "light-emitting diode-LED" as used herein also includes laser diodes.

LEDs in the devices according to the invention may be operated in a pulsed mode or modulated mode to vary the output radiation intensity to suit the application, and multiple clusters of LEDs, such as in the embodiment of FIG. 6, may each be generated in a different mode.

The power supply for the LEDs of the device according to the invention could be mains power, battery power, capacitor, supercapacitor, solar power, clockwork generator or generator powered by the mechanical effort of the operator or assistant.

In one embodiment, a capacitor or supercapacitor could be used to power the array having advantages over conventional rechargeable sources such as batteries. Capacitors can be virtually instantaneously recharged between one or more curing cycles of operation when the unit is connected to a power source.

The power supply for the device may be re-chargeable, and may be designed to make automatic electrical contact with the charging means of a base unit when engaged with the latter in the manner of a cordless telephone handset.

What is claimed is:

1. An optical irradiation device comprising an array of light-emitting diodes (LEDs) clustered so that radiation they emit is directed into a beam characterised in that each LED is formed with multiple facets such that the facets of adjacent LEDs adjoin one another in close proximity throughout their length, wherein heat is removed from the LEDs by a heat pipe.

2. A device as claimed in claim 1 in which the facets of adjacent LEDs extend substantially parallel to one another.

3. A device as claimed in claim 1 in which the facets of adjacent LEDs abut one another.

4. A device as claimed in claim 1 in which LEDs are arranged in a ring with side facets of adjacent LEDs adjoining one another.

5. A device as claimed in claim 4 in which LEDs are arranged in concentric rings with side facets of adjacent LEDs in each ring adjoining one another.

6. A device as claimed in claim 5 in which the LEDs of adjacent rings have radially directed facets adjoining one another.

7. A device as claimed in claim 4 in which a single LED is located within said ring or innermost concentric ring.

8. A device as claimed in claim 7 in which said single LED has radially directed facets that adjoining facets of the LEDs in said ring or innermost concentric ring.

9. A device as claimed in claim 1 in which the LEDs are regular polygons in cross-section.

10. A device as claimed in claim 9 in which the LEDs are hexagonal in cross-section.

11. A device as claimed in claim 1 in which the facets of the LEDs are polished.

12. A device as claimed in claim 1 in which the facets of the LEDs are provided with a reflective coating.

13. A device as claimed in claim 1, including a light guide for collecting light from the cluster of light emitting diodes.

14. A device as claimed in claim 1, wherein a light guide is provided for each light emitting diode in the cluster.

15. A device as claimed in claim 1 including a light guide for collecting light from the cluster of LEDs, the light guide having an index that vanes from one par to another so as to manpulate the light.

16. A device as claimed in claim 1 including a light guide that consists of a few fibres formed individually before being bundled together.

17. A device as claimed in claim 1 including a light guide consisting of shaped fibres packed together so that the packing fraction is reduced.

18. An irradiation device employing LEDs and a tapered light guide to collect radiation emitted by the LEDs and deliver this to an output beam, characterised in that two or more tapered light guides are arranged in series so that successive guides receive radiation from preceding guides, and an LED or group of LEDs is provided at the input end of each guide, wherein each successive guide is provided with a ring of LEDs around the output end of the preceding guide.

19. A device as claimed in claim 1 in which a plurality of heat pipes is used to transfer heat from the LEDs.

20. A device as claimed in claim 1 in which an annular heat pipe is used so that it can contain energy storage means.

21. A device as claimed in claim 1, including a Peltier device to cool the LEDs.

22. A device as claimed in claim 1 having a pistol grip to contain energy storage means.

23. A device as claimed in claim 1, including a capacitor or supercapacitor to power the device.

24. A hand-held device for curing dental materials including an optical irradiation device as claimed in claim 1.

25. An irradiation device employing LEDs and a tapered light guide to collect radiation emitted by the LEDs and deliver this to an output beam, characterised in that at least three tapered light guides are arranged in series so that successive guides receive radiation from each of the preceding guides, and an LED or group of LEDs is provided at the input end of each guide.

26. A device as claimed in claim 25 in which each successive guide is provided with a ring of LEDs around the output end of the preceding guide.

* * * * *